US012544290B2

(12) United States Patent
Bernardoni et al.

(10) Patent No.: US 12,544,290 B2
(45) Date of Patent: Feb. 10, 2026

(54) APPARATUS FOR POSITIONING A LOWER LIMB OF A PATIENT DURING SURGERY AND SURGICAL POSITIONING SYSTEM COMPRISING SAID APPARATUS

(71) Applicant: MEDACTA INTERNATIONAL SA, Castel San Pietro (CH)

(72) Inventors: Massimiliano Bernardoni, Castel San Pietro (CH); Francesco Siccardi, Castel San Pietro (CH); Ermete Rossi, Castel San Pietro (CH); Mirko Giardiello, Castel San Pietro (CH); Frederic Laude, Paris (FR)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 572 days.

(21) Appl. No.: 17/920,600

(22) PCT Filed: Apr. 20, 2021

(86) PCT No.: PCT/IB2021/053229

§ 371 (c)(1),
(2) Date: Oct. 21, 2022

(87) PCT Pub. No.: WO2021/214643

PCT Pub. Date: Oct. 28, 2021

(65) Prior Publication Data

US 2023/0149241 A1 May 18, 2023

(30) Foreign Application Priority Data

Apr. 24, 2020 (IT) ........................ 102020000008854

(51) Int. Cl.
*A61G 13/12* (2006.01)
*A61F 5/37* (2006.01)

(52) U.S. Cl.
CPC .......... *A61G 13/123* (2013.01); *A61F 5/3769* (2013.01); *A61G 13/128* (2013.01)

(58) Field of Classification Search
CPC ...... A61G 13/12–1255; A61G 13/0063; A61G 13/0081; A61G 7/109–1098;
(Continued)

(56) References Cited

U.S. PATENT DOCUMENTS 5,961,085 A * 10/1999 Navarro ................ A47C 16/00 5/624
2003/0028967 A1 2/2003 Schuerch
(Continued)

FOREIGN PATENT DOCUMENTS

EP 3017801 A1 5/2016
JP 2002514110 A 5/2002
(Continued)

OTHER PUBLICATIONS

Notice of Reasons for Refusal received in connection with Japanese Application No. 2022564121, dated Oct. 17, 2023, 11 pages.
(Continued)

*Primary Examiner* — Adam Baker
(74) *Attorney, Agent, or Firm* — Meunier Carlin & Curfman LLC

(57) ABSTRACT

An apparatus for positioning a lower limb of a patient during surgery comprises at least one support structure connectable, through a proximal end, to a support device for a patient and defining a traction axis of the patient's lower limb, a traction slide slidingly movable on the support structure, a gripping body for a distal end of the patient's lower limb connectable to the traction slide. The support structure, when connected to the support device for a patient, is suspended and comprises at least one actuator, hydraulically connected with the traction slide, for moving the support structure in space.

23 Claims, 11 Drawing Sheets

(58) Field of Classification Search
CPC .. A61H 1/0218; A61H 1/0222; A61H 1/0237; A61H 1/024; A61H 1/0255; A61H 1/0274–0285; A61F 5/04; A61F 5/042; A61F 5/048; A61F 5/3761
USPC .......................................................... 128/882
See application file for complete search history.

(56) References Cited

U.S. PATENT DOCUMENTS

| | | | | |
|---|---|---|---|---|
| 2007/0265635 | A1* | 11/2007 | Torrie .................. | A61G 13/123<br>606/105 |
| 2011/0023893 | A1* | 2/2011 | Striggow ........... | A61G 13/0081<br>128/882 |
| 2014/0068866 | A1* | 3/2014 | Catacchio .............. | A61G 7/075<br>5/630 |
| 2016/0120726 | A1* | 5/2016 | Moriarty ............ | A61G 13/0036<br>5/649 |
| 2017/0281447 | A1* | 10/2017 | Lane, II ............. | A61G 13/1235 |
| 2019/0254905 | A1* | 8/2019 | Lane, II ............. | A61G 13/1295 |
| 2021/0145684 | A1* | 5/2021 | Schuerch ............. | A61G 13/101 |

FOREIGN PATENT DOCUMENTS

| | | | |
|---|---|---|---|
| WO | 9844890 | A1 | 10/1998 |
| WO | 2014043538 | A1 | 3/2014 |
| WO | 2014045199 | A1 | 3/2014 |
| WO | 2019220239 | A1 | 11/2019 |

OTHER PUBLICATIONS

International Search Report and Written Opinion issued in PCT/IB2021/053229, mailed Jun. 21, 2021, 8 pages.

* cited by examiner

APPARATUS FOR POSITIONING A LOWER LIMB OF A PATIENT DURING SURGERY AND SURGICAL POSITIONING SYSTEM COMPRISING SAID APPARATUS

FIELD OF APPLICATION

The present invention relates to an apparatus for positioning a limb, in particular the lower limb, of a patient during surgery and a surgical positioning system comprising said apparatus.

The apparatus subject matter of the present invention applies to the field of orthopaedic surgery and finds useful application especially in hip replacement operations with anterior approach and in arthroscopic operations.

PRIOR ART

The prior art proposes various surgical techniques for the partial or total replacement of a patient's hip prosthesis.

A now widely used technique, particularly appreciated for its low invasiveness and known under the trade name AMIS®, envisages an anterior approach that reaches the hip joint passing through the intermuscular plane between the tensor fasciae latae and the sartorius/rectus femoris. For a correct execution of this technique, however, it is necessary to perform a series of manipulations of the lower limb of the patient, so as to allow the surgeon to operate always in conditions of optimal access to the surgical site.

In this case, the limb of the patient positioned in supine decubitus must be first placed in light traction to facilitate an initial capsulotomy operation. Traction should then be slightly increased before the next osteotomy operation of the femoral neck. Once the osteotomy has been performed, further traction and subsequent external rotation of the joint is applied to allow extraction of the severed femoral head. Traction is then released on the limb before the acetabulum is milled and the replacement cup is placed. To prepare for the introduction of the femoral prosthesis, traction is again applied, then external rotation is performed at more than 90°, traction is released, the limb is hyperextended and brought into adduction. The limb is then returned to its original position before suturing.

As is readily apparent from the brief description of the surgical technique provided above, the number and the precision of the manipulations to be performed need the use of an auxiliary apparatus for positioning the lower limb.

Although the positioning devices known to date substantially meet the needs of the sector, they nevertheless have a number of unresolved drawbacks.

Firstly, it is noted that such devices must be operated by a dedicated operator. In addition to the surgeon and the instrumentalist, an additional person is required in the operating room, which increases the cost of the surgery. In addition, the need to delegate to a third-party operator the operations for moving the lower limb can lead to an inconvenience for the surgeon, who is forced to coordinate his intervention with that of another person.

To address these problems WO 2014/045199, on behalf of the same Applicant, proposes an apparatus in which the traction and extension axes are controlled by actuators, preferably of the pneumatic type. By means of a control pedal, the surgeon can suitably operate the actuators to cause the traction and extension movement of the limb, during the various phases of the operation.

Even this solution, however, is not free of drawbacks related mainly to the weight and bulk of the apparatus that, in order to be assembled on the operating table, requires more people or dedicated secondary equipment. Moreover, due to the high weight of the structure, the apparatus has resting legs and feet that hinder the movement of the surgeon and of the personnel in charge of moving the apparatus itself around the operative site. In addition, the apparatuses currently used, precisely because they rest on the ground, do not offer the surgeon the possibility of being moved easily and freely in space, especially in height.

The currently known lower limb positioning apparatuses have complex retention mechanisms of the possible movements, such as traction and rotation, which must first be unlocked by the operator in order to allow the movement of the limb, thus making the surgical procedure less smooth.

The Applicant has also found that at the end of the AMIS® surgery it is often difficult to return the operated leg to the same position of the pre-operative phase as regards the extension of the leg (following extension/traction movements) and its rotation (following abduction/adduction); it is fundamental to verify that the leg is repositioned in the same initial condition in order not to cause discomfort to the patient. Therefore, having a comparison with the pre-operative position of the leg itself is essential.

The technical problem underlying the present invention is, therefore, that of devising a positioning apparatus which solves the drawbacks described in the prior art, and which is structurally light, not bulky and, in particular, sufficiently manoeuvrable by the surgeon alone.

A further object of the present invention is to propose a positioning apparatus which provides simple-to-use movement mechanisms and which allows the surgeon a smooth movement of the structure and, therefore, of the limb.

Finally, it is an object of the present invention to provide a positioning apparatus which offers a precise and simple verification of the correct position of the leg and a rapid comparison with the pre-operative position of the operated leg.

These and other objects are achieved by an apparatus for positioning a lower limb of a patient during surgery as described in the appended claims and by a surgical positioning system comprising said apparatus.

SUMMARY OF THE INVENTION

In particular, according to a first aspect, the present invention relates to an apparatus for positioning a lower limb of a patient during surgery comprising at least one support structure, defining a traction axis of the lower limb, connectable, through a proximal end, to a support device for a patient; a traction slide, slidingly movable on the support structure; and a gripping body for a distal end of the patient's lower limb connectable to the traction slide. The support structure, when connected to said support device for a patient, is suspended and comprises at least one actuator, hydraulically connected with the traction slide to move the support structure in space. The actuator comprises an internal excursion locking system.

The traction slide further comprises a handle and a lever system capable of unlocking the sliding of the slide along the support structure, with a first command activable by bringing the lever system from a locking position to a first unlocking position, and of releasing the excursion locking system of the actuator with a second command activable by bringing the lever system to a second unlocking position, so as to achieve an automatic unlocking and the movement in space of the support structure.

The support structure comprises a central support bar, developing in a straight line along a longitudinal development axis, coinciding with the traction axis of the lower limb, which has a sliding guide for the traction slide. The support structure further comprises a portion for the connection to a support device for a patient, placed at a proximal end of the central bar and extending transversely with respect thereto. The actuator extends from the connection portion up to the central bar and thus defines an isostatic polygonal structure.

The traction slide is, moreover, bound to one or more skids sliding on the sliding guide mounted on the central bar.

The sliding guide has a plurality of holes aligned along the longitudinal axis of the central support bar; the holes have respective central axes parallel to each other. A tip inside the slide engages one of these holes to lock the movement of the traction slide along the sliding guide.

The lever system comprises a release lever that can assume three different positions; a rest or translation locking position of the slide, a first translation unlocking position of the slide, at which the first command is activated, and a second unlocking position in the space of the support structure, at which the second command is activated. The three positions are arranged in sequence. The commands that cause the movement of the translation slide to be unlocked and the rotational movement to be unlocked in the space of the support structure can therefore be activated in sequence.

The lever system further comprises a tip, slidingly movable along a vertical direction, orthogonal to the longitudinal axis of the support bar. The release lever, at its first unlocking position, acts on the tip to disengage it from a respective hole of the plurality of holes present in the sliding guide and to allow the translation of the slide along the sliding guide. All of this occurs following the activation of the first command.

The lever system further comprises a release system activable by the release lever at its second unlocking position, subsequent to the first unlocking position; the release system interacts with the internal excursion locking system of the actuator to unlock the spatial movement of the support structure. All this occurs following the activation of the second command.

The central support bar has, on at least one side, a graduated scale for detecting the position of the traction slide along the support bar and establishing the length of the lower limb in the pre-operative position. This measurement is used to restore the correct position and alignment of the limb at the end of the operation.

The apparatus further comprises a plurality of double joints placed between the central bar and the connection portion, between the connection portion and the actuator, and between the actuator and the central bar. These double joints allow the support structure to make the appropriate rotational movements in space and to allow the traction slide to translate along the sliding guide.

The actuator comprises at least one fluid spring, preferably two gas springs. The actuator, and therefore the fluid spring, is provided with an internal excursion locking system, to lock the excursion of the actuator, and therefore of the support structure, when its movement in space is not required.

The apparatus also comprises a rotation group associable to the traction slide and connectable to the gripping body; the rotation group has a first and a second configuration, alternatively or simultaneously implementable depending on the surgical procedure to be performed and/or whether the apparatus is associated with a limb to be operated or not operated on.

Furthermore, the rotation group according to the first configuration is preferably used in the hip joint replacement surgery through mini-invasive approach AMIS® (or DAA direct anterior approach), in order to manage the operated limb, while the rotation group according to the second configuration is advantageously used in the hip joint replacement surgery through mini-invasive approach AMIS® (or DAA direct anterior approach), in order to support the non-operated limb, commonly referred to as “contralateral” and in arthroscopic surgical procedures.

The rotation group, according to the first configuration, is adapted to rotate the lower limb of the patient in a continuous manner and according to a pitch at will established by the surgeon during the operative phase, in an internal or external direction with respect to the sagittal axis of the patient, that is in an internal or external direction with respect to the traction axis.

The rotation group, in the first configuration, comprises a main body for the connection to the traction slide, an oscillating group allowing the rotation group, connected to the traction slide, to adapt to the natural position and inclination of the lower limb, a command handwheel manoeuvrable by the surgeon, a rod capable of transmitting the rotation from the command handwheel to the gripping body of the lower limb, a connection hook, rigidly connected to an end of the rod, for connecting the rotation group to the gripping body of the lower limb, and a graduated ring nut for detecting the rotation angle applied to the lower limb.

In addition, the positioning apparatus comprises a fine traction mechanism, for the millimetric movement in traction of the lower limb, connectable to the gripping body of the distal end of the lower limb and supported by the traction slide.

The fine or millimetric traction mechanism comprises a rod which is connectable to the gripping body by means of the aforementioned connection hook and is supported by the traction slide by means of the aforementioned oscillating group that allows the connection to the traction slide: in this way, the rod adapts to the position and the natural inclination of the lower limb. The fine or millimetric traction mechanism further comprises a command element for activating the millimetric translation of the gripping body with respect to the traction slide and with respect also to the support structure, when the traction slide is fixed with respect to the support structure.

The fine traction mechanism also comprises a threaded bar screwable into the rod. The command element rotates the threaded bar in order to promote the screwing with the rod and thus cause the translation of the latter and of the gripping body with respect to the traction slide.

The rod of the fine traction mechanism is graduated and slides through the rotation group, in accordance with the first configuration.

The rotation group, in accordance with the second configuration, is adapted to rotate the lower limb of the patient in a discrete manner, according to a predetermined angular pitch, in an internal or external direction with respect to the sagittal axis of the patient, that is, in an internal or external direction with respect to the traction axis.

In this second configuration, the rotation group comprises an oscillating body, connected to the traction slide by means of a rotating pin, a rotation shaft rotationally connected to the oscillating body and carrying, at a free end, a connection hook for connecting the rotation group to the gripping body of the distal end of the lower limb, a manoeuvring organ, connected to the rotation shaft, capable of rotating the rotation shaft according to a predefined angular pitch, and a locking pin, engaged with the manoeuvring organ, adapted to lock and unlock the movement of the manoeuvring organ.

The support structure comprises, at a distal end, at least one wheel for moving the apparatus in a pre-operative set up phase. This wheel allows the movement of the entire apparatus, which does not have any other point resting on the ground and of support, and to bring it closer to the operating table to then lift it and connect it, in suspension, to the table or to the resting plane of the patient.

The portion for connecting the apparatus to a support plane for a patient has a quick coupling to facilitate the hooking and unhooking operations of the apparatus.

In accordance with a second aspect, the present invention also relates to a surgical positioning system comprising a positioning apparatus according to what is described in the foregoing and a support device for a patient, coupled to the positioning apparatus through at least one bracket for connecting and stiffening the support device.

The support device for a patient may be a surgical table or an adapter plane arranged to cover a surgical table.

Further features and advantages will appear more from the detailed description made below of two preferred, but not exclusive, embodiments of the present invention, with reference to the united figures given by way of non-limiting example.

BRIEF DESCRIPTION OF THE DRAWINGS

The present invention will be made clearer by the following detailed description, with reference to the accompanying drawings provided by way of example only, wherein.

DETAILED DESCRIPTION

In the aforementioned figures, an apparatus for positioning a lower limb of a patient during surgery in accordance with the present invention has been collectively referred to as 1.

The positioning apparatus 1, which is the subject matter of the present invention, can be used in the hip joint replacement surgical procedure through mini-invasive approach AMIS® (or DAA direct anterior approach) and in the surgical procedure of hip arthroscopy.

Further, the positioning apparatus 1 may be used either on a limb to be operated on, as a support and positioning means, or on a limb not to be operated on, as a support means only.

Depending on the specific use and the surgical procedure used, the apparatus presents a different configuration as will be explained below.

Figure 7:
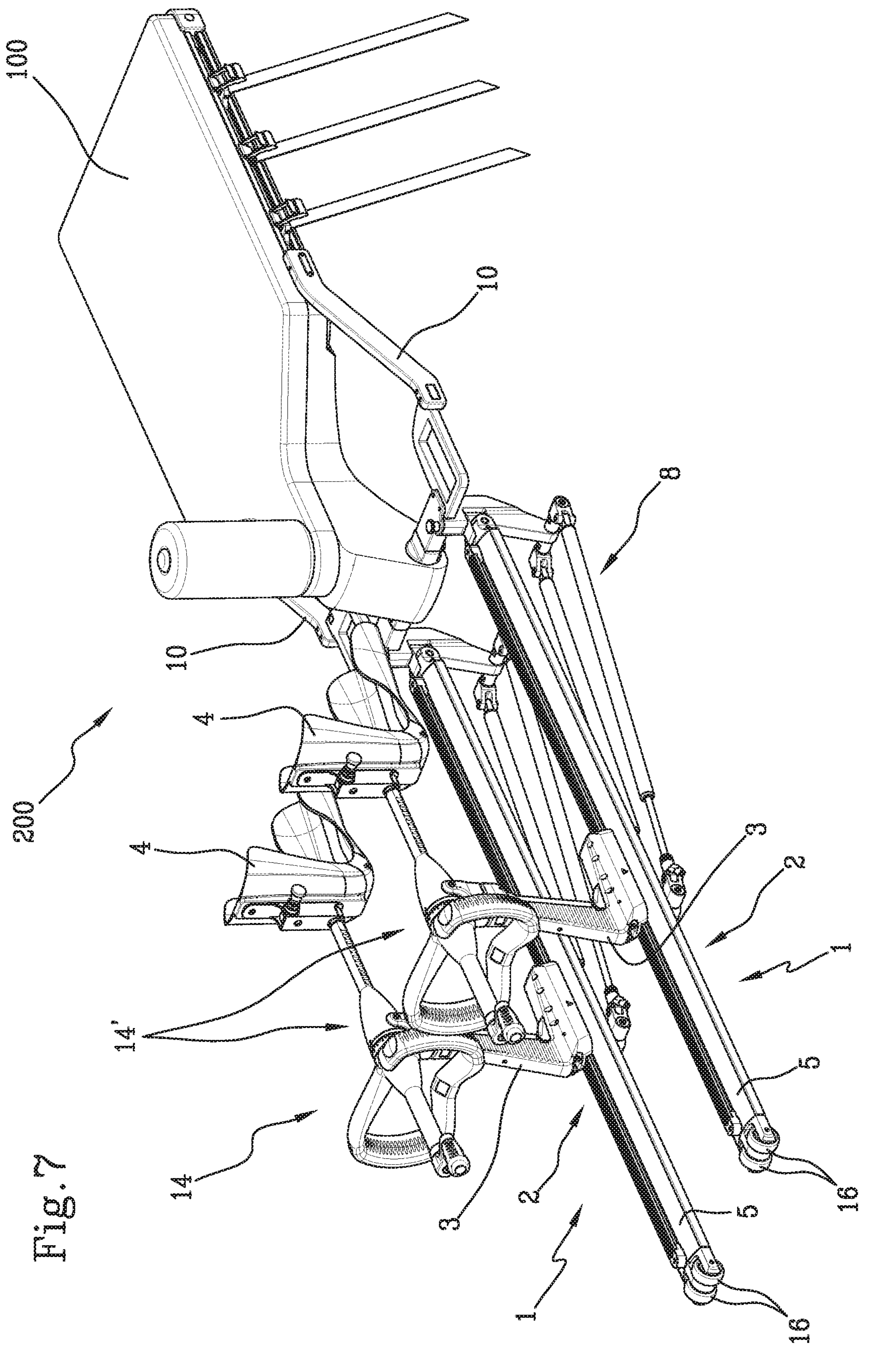
FIG. 7 illustrates a perspective view of a surgical positioning system subject matter of the present invention, in accordance with a first constructive configuration.
Figure 8:
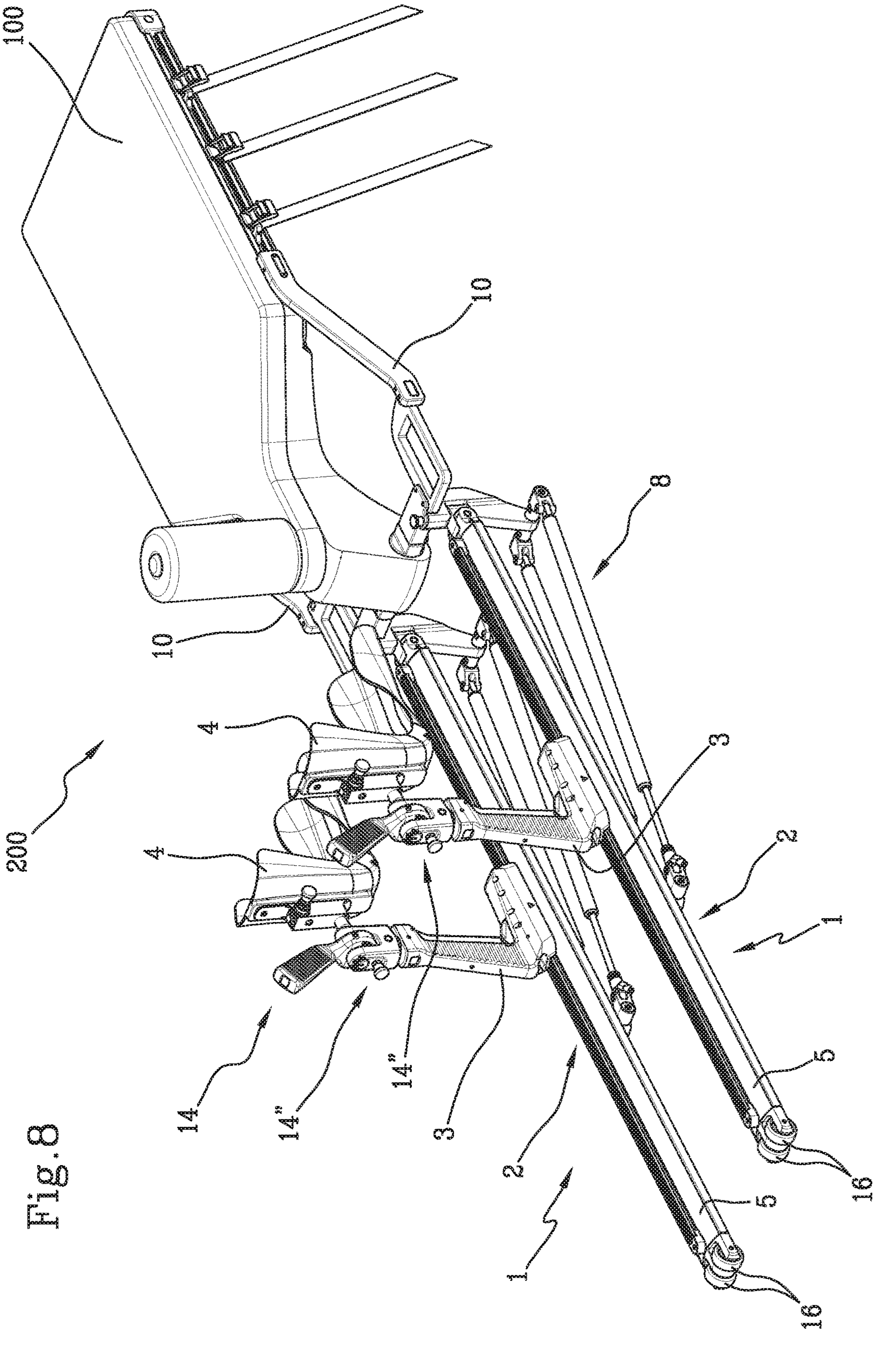
FIG. 8 illustrates a perspective view of a surgical positioning system subject matter of the present invention, in accordance with a second constructive configuration.
Figure 9:
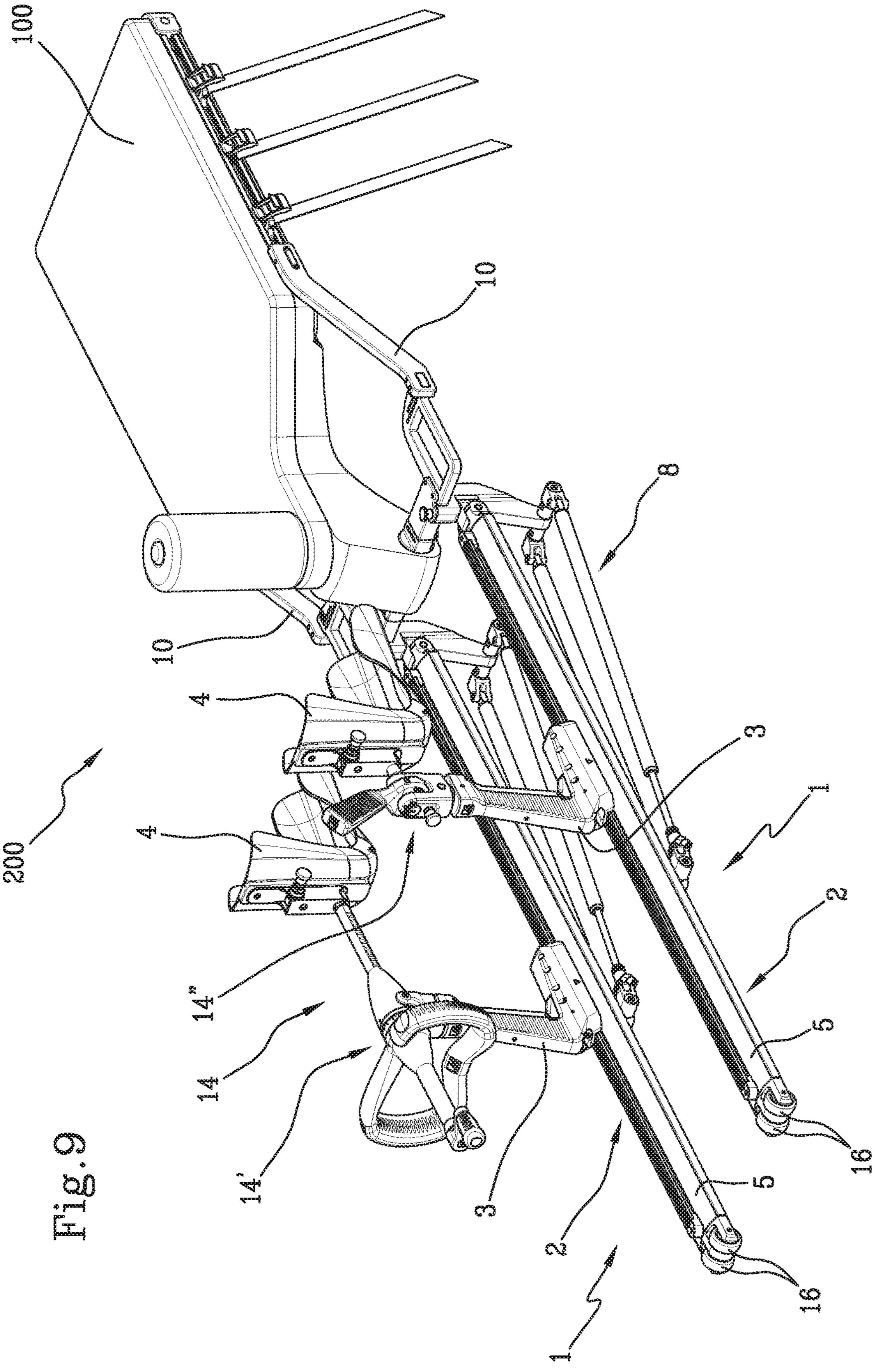
FIG. 9 illustrates a perspective view of a surgical positioning system subject matter of the present invention, in accordance with a third constructive configuration.

The positioning apparatus 1 is integrated into a surgical positioning system 200, which generally has two positioning apparatuses 1, one per leg. Depending on the surgical operation to be performed and the combination of the two types of apparatuses, there may be different configurations of the positioning system 200 as well, as illustrated in FIGS. 7, 8 and 9 and as will be explained in detail below.

Specifically, the device is used on the leg to be operated in the hip joint replacement surgical procedure through mini-invasive approach AMIS® (or DAA direct anterior approach) and, eventually, also as a support/positioning of the non-operated limb during the same surgical procedure, or as a means of support/positioning during arthroscopic surgical procedures.

The positioning apparatus 1 according to the present invention comprises at least one support structure 2 connectable, through a proximal end 2*p*, to a support device 100 for a patient. Advantageously, the support device 100 for a patient is a surgical table or an adapter table arranged to cover, at least partially, a surgical table.

The support structure 2 develops along a traction axis X of the patient's limb.

The apparatus 1 further comprises a traction slide 3 for the limb to be moved, slidingly movable on the support structure 2 and to which a gripping body 4 for a distal end (the foot) of the patient's lower limb is connectable. Specifically, the gripping body 4 may be a kind of boot or brace that wraps around the foot, to transmit the traction or rotation movement to the entire limb, without causing trauma to the limb itself or to the foot.

Figure 1:
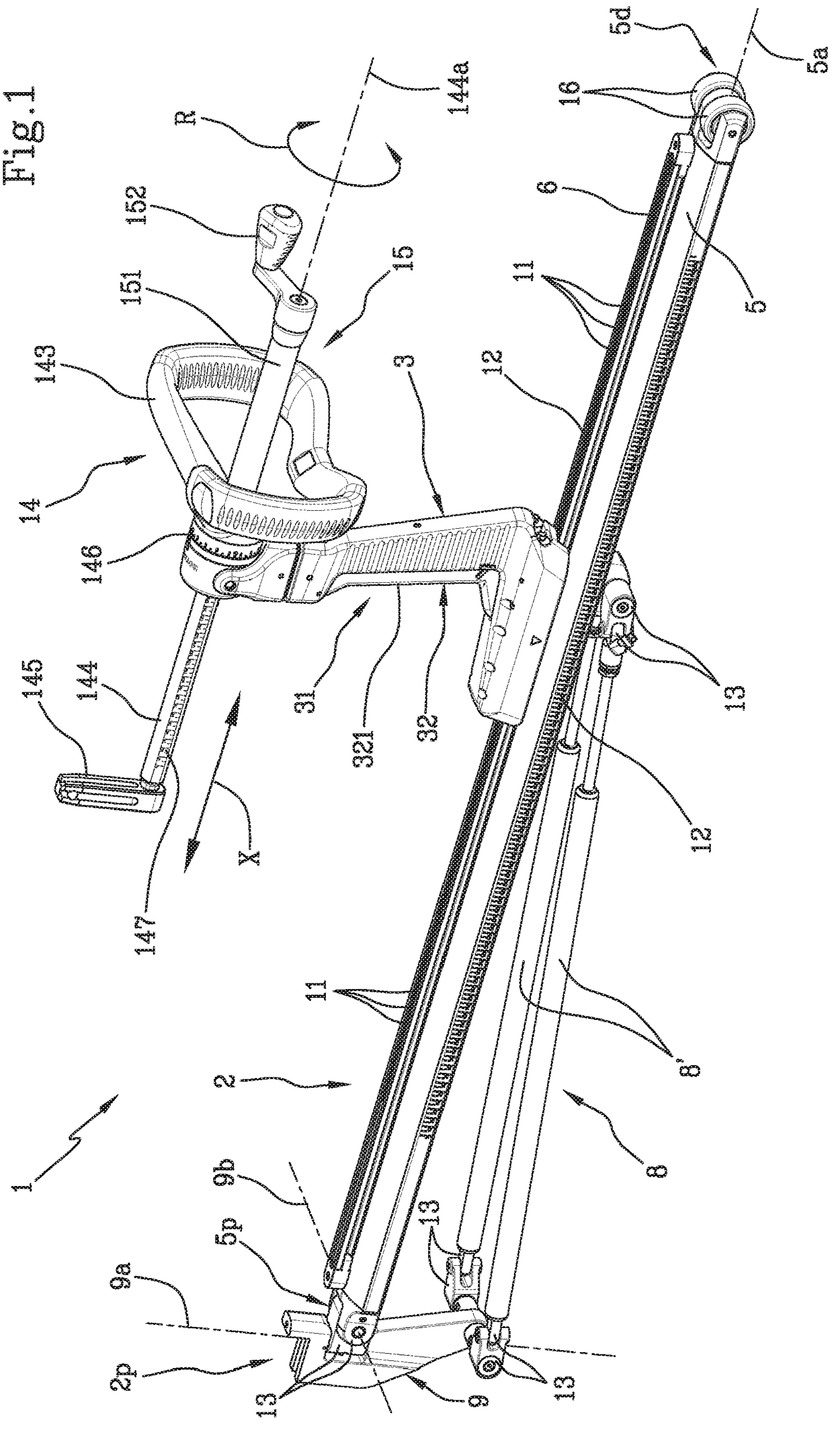
FIG. 1 illustrates a perspective view of an apparatus for positioning a lower limb of a patient in accordance with the present invention, according to a first configuration.
Figure 2:
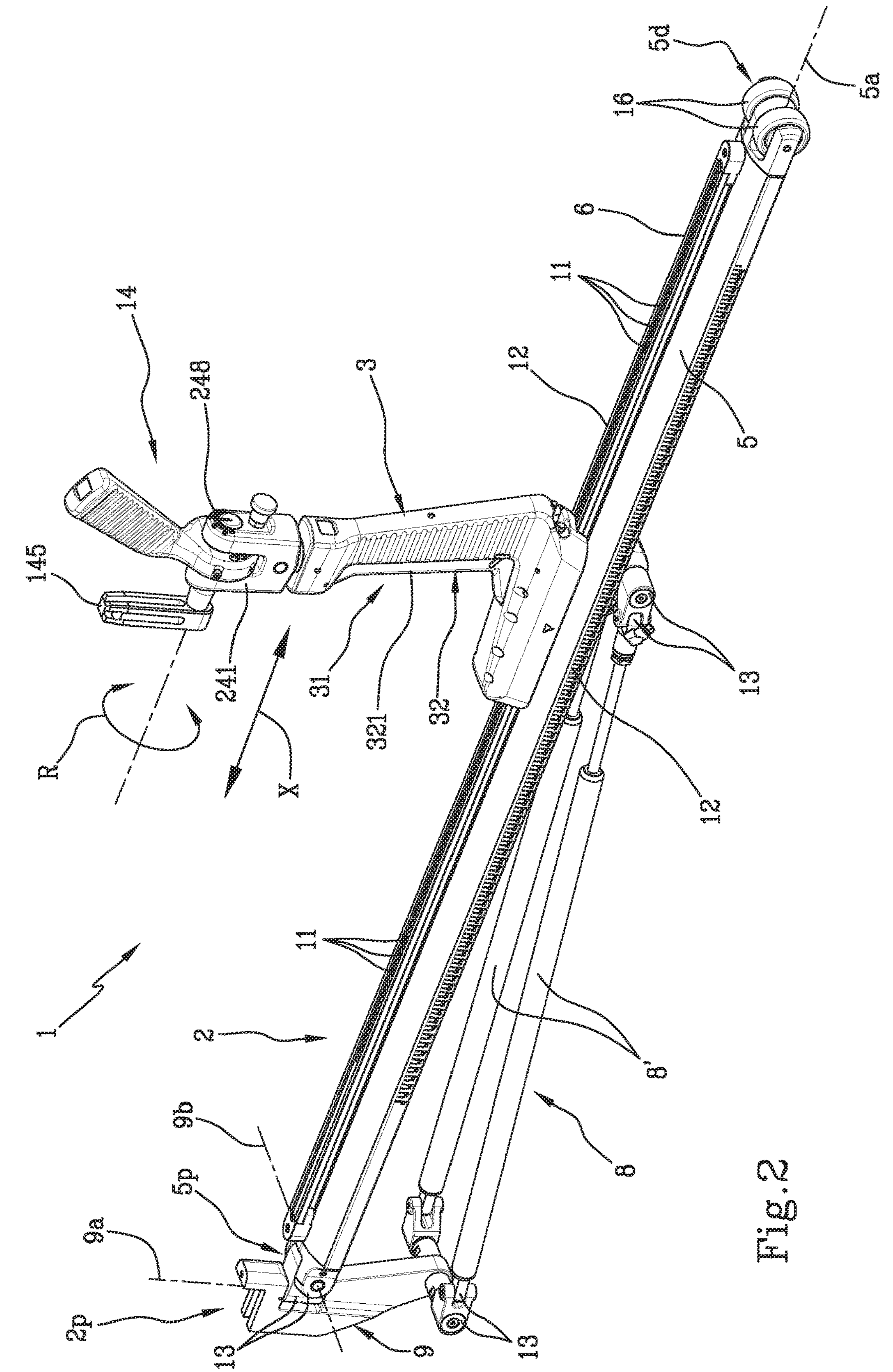
FIG. 2 illustrates a perspective view of an apparatus for positioning a lower limb of a patient in accordance with the present invention, according to a second configuration.

As shown in FIG. 1 or 2, the support structure 2 comprises a central support bar 5, developing in a straight line along a longitudinal axis 5*a*, parallel to the traction axis X. The central support bar 5 has a sliding guide 6 for the traction slide 3.

In particular, the traction slide 3 is bound to one or more skids 7 (visible in FIGS. 3A-3C), sliding on the sliding guide 6, mounted on the central bar 5.

On at least one side of the central support bar 5 there is positioned a graduated scale 12 adapted to detect the position of the traction slide 3 along the support bar 5 itself, and to establish the length of the lower limb in a pre-operative position. Advantageously, there are two graduated scales 12, one on each side of the central support bar 5.

The support structure 2 further comprises at least one actuator 8, hydraulically connected to the traction slide 3, for moving the entire support structure 2 in space.

Preferably, the actuator 8 comprises at least one fluid spring, for example a gas spring 8'. In the configuration shown, two gas springs 8' are provided. Advantageously, the actuator 8 comprises an internal excursion locking system, specifically a stem excursion locking system 8' of the fluid (preferably gas) spring.

The support structure 2, when connected to the support device for the patient, is suspended, i.e., it does not rest on the ground in any way, but it is supported only by the connection to the device (resting plane or table) on which the patient lies.

Thus, there are no legs resting on the floor and projecting downward from the support structure to support the apparatus 1 both during the use thereof in the operative phase and when not in use.

In this regard, there is provided, at a proximal end 5*p* of the central support bar 5, a connection portion 9 for binding the support structure 2 to a support device 100 for a patient. Said connection portion 9 extends transversely with respect to the central bar 5 and can be bound to a connecting and stiffening bracket 10.

As visible in FIG. 7, 8 or 9, a connecting and stiffening bracket 10 is provided on each side of the support device 100 for a patient, each having the purpose of stiffening the structure of the device 100 on which the patient is lying, as well as mounting the components that support the patient's thigh, in the case of a prosthetic surgical procedure of the hip (not shown).

At the distal end 5*d* the support bar 5, and thus the support structure 2, has at least one wheel 16, preferably two, which is used to move the apparatus 1 in the pre-operative set up phase, thus to displace and bring the apparatus in proximity to the resting device 100 and then to be mounted on the latter. Once connected to the resting device 100, the apparatus 1 remains suspended, bound to the resting device 100 only by the connection portion 9 connected to the bracket 10, without any further points resting on the floor. In this way, the apparatus 1 results, as a whole, a very compact structure, without non-essential protrusions that project into the underlying area and that, in the operative phase, may hinder the movement of the surgeon.

The actuator 8 extends between the connection portion 9 and the central bar 5 to define a polygonal structure. More in detail, the actuator 8 is connected on one side to the traction slide 3, in particular to the skids 7, below the central bar 5, and on the other side to the end of the connection portion 9 opposite to the binding portion with the central bar 5. The connection to the traction slide 3 causes the translation of the latter to elongate or shorten the stem of the gas springs 8' of the actuator 8.

As shown in FIGS. 1, 2 and 3, the traction slide 3 comprises a handle 31, which acts as the structure of the slide itself, and a lever system 32, capable of unlocking the sliding of the slide 3 along the support structure 2, with a first command, and of releasing the locking system of the actuator, with a second command, so as to achieve an automatic unlocking of the traction, that is, to achieve the unlocking in the space of the support structure 2 and to allow, therefore, its free spatial movement.

In other words, the traction system 3 is a single command organ for both the translation of the limb to be moved and the rotational movement in space of the entire support structure 2.

With only the control and command of the traction slide 3, which is made as a sort of joystick in the preferred and illustrated configuration, the surgeon can easily grasp and move the traction slide itself along the axis 5*a* of the central support bar and then along the sliding guide 6, and can also move rotationally, along determined axes, the entire support structure 2 in order to position it in the most suitable way for him for carrying out the different operative phases. This is made possible by both the connection of the traction slide 3 on the sliding guide 6 and the fluid connection between the actuator 8 and the traction slide 3 itself.

The rotation of the support structure 2 occurs about vertical 9*a* and horizontal 9*b* hinge axes, passing through a plurality of double joints 13 present between the central support bar 5 and the portion 9 for connecting the support structure 2 to a support device 100 for a patient, as will be explained below.

The surgeon is therefore able to activate the translation of the patient's limb along the axis 5*a* of the central support bar 5 and to unlock the rotational movement in space of the entire support structure 2 by acting only on the traction system 3. This is done by means of the handle 31 and the lever system 32 which, as described above, unlocks the sliding of the traction system 3 along the sliding guide 6 by means of a first command, activated by applying a certain pressure force on the lever system 32; by subsequently applying a greater pressure force on the lever system 32, a second command is activated which releases the system for locking the movement of the gas springs 8' of the actuators 8, in fluid connection with the traction system 3, thus allowing the rotational movement of the support structure 2 in space.

Figure 3A:
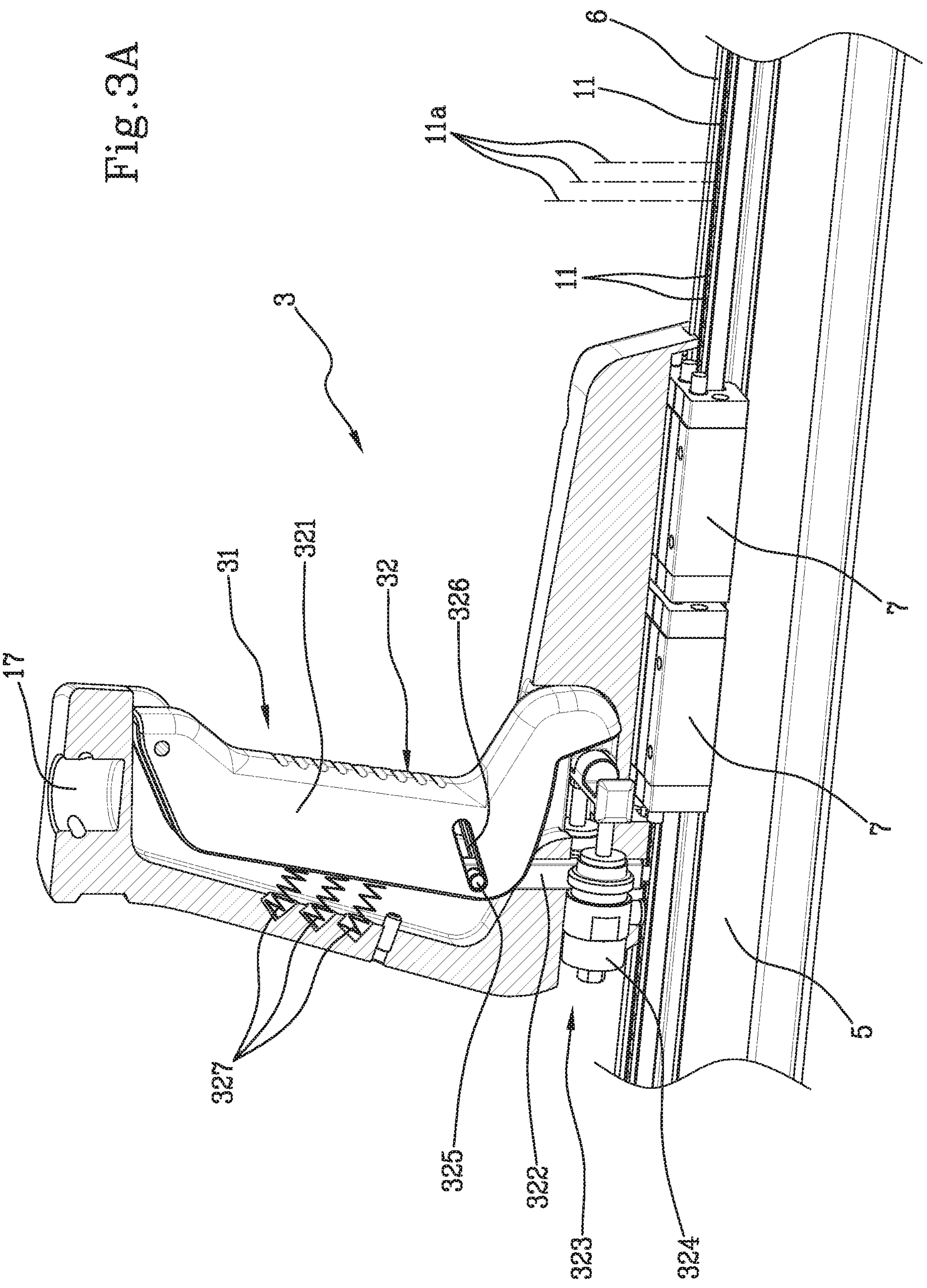
FIG. 3A illustrates a perspective view, partially sectioned along a longitudinal axis parallel to the traction axis X, of the apparatus subject matter of the present invention, with the rotation group removed to better highlight some details and with the release lever in a locking or rest position.
Figure 3B:
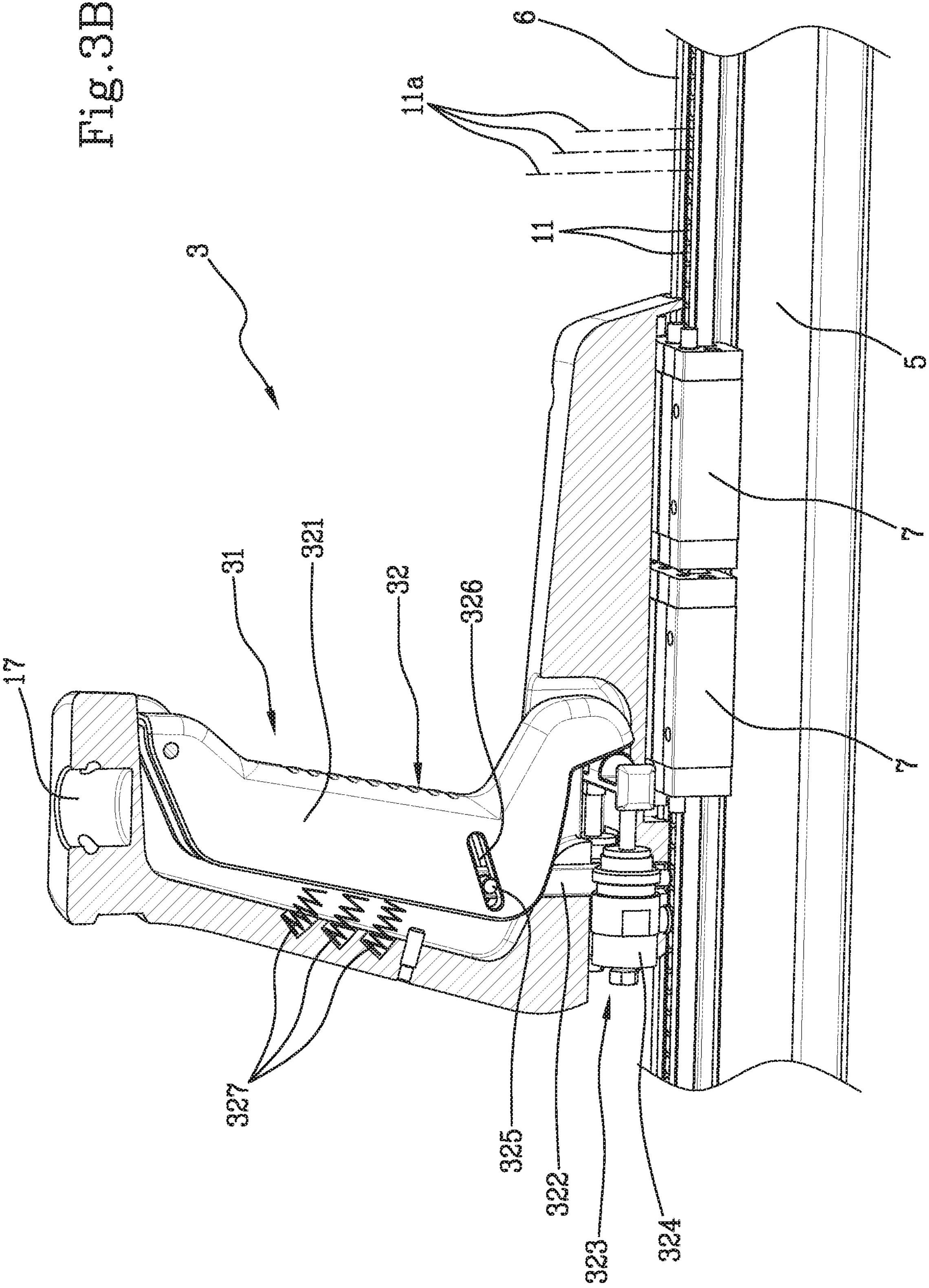
FIG. 3B illustrates a perspective view, partially sectioned along a longitudinal axis parallel to the traction axis X, of the apparatus subject matter of the present invention, with the rotation group removed to better highlight some details and with the release lever in a first translation unlocking position of the slide.
Figure 3C:
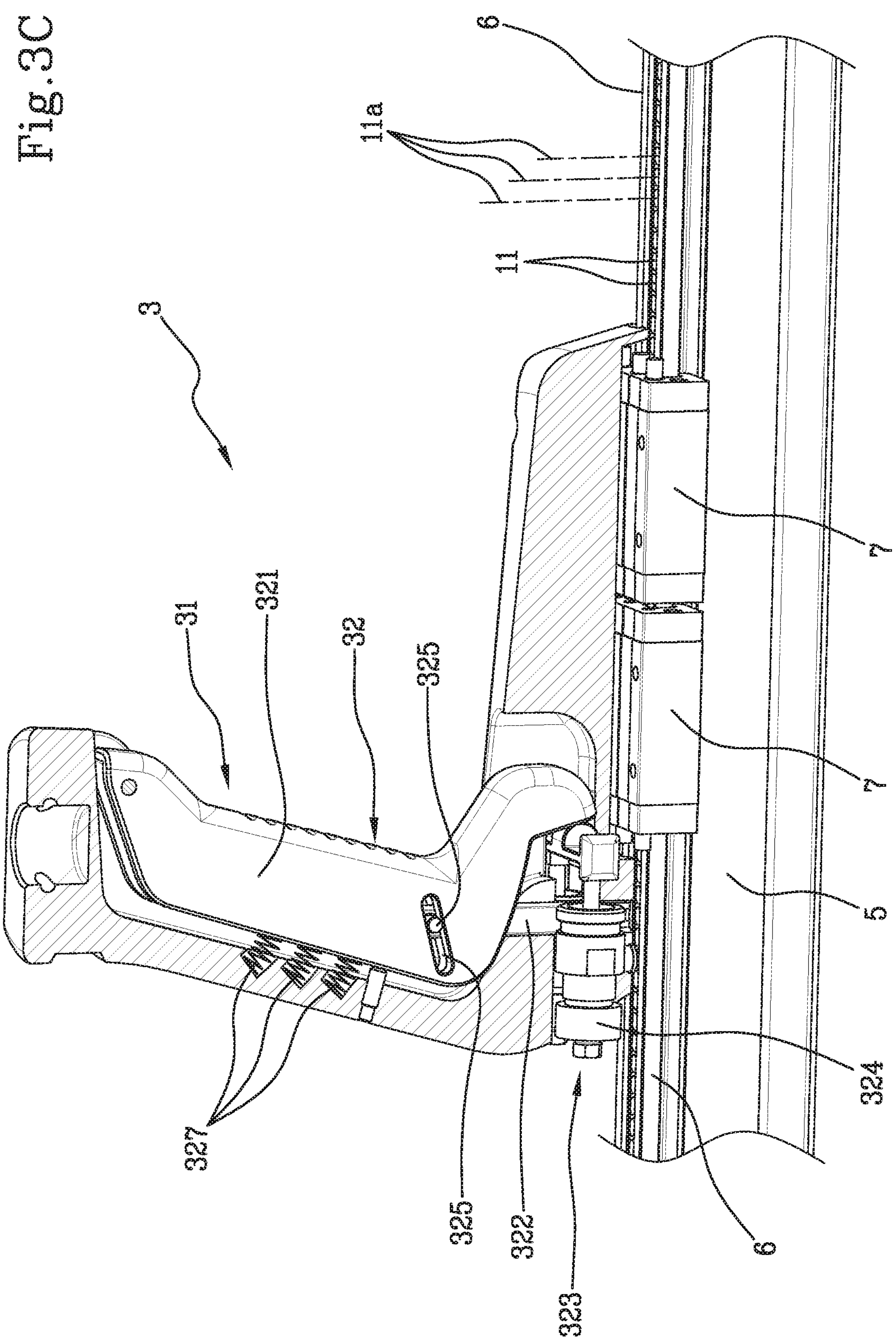
FIG. 3C illustrates a perspective view, partially sectioned along a longitudinal axis parallel to the traction axis X, of the apparatus subject matter of the present invention, with the rotation group removed to better highlight some details and with the release lever in a second unlocking position in the space of the support structure.

Going into detail about this structure, the lever system 32 comprises a release lever 321 that can assume (as shown in FIG. 3A) a translation locking position of the slide 3 (or rest position), at which any movement of the traction slide 3 along the sliding guide 6 is prevented. At this locking position, any movement in space of the whole support structure 2 is also prevented.

The release lever 321 may assume a first translation unlocking position of the slide 3 (FIG. 3B), at which the aforementioned first command is activated. In other words, by acting on the handle 31 and pressing on the release lever 321, up to a first end stop, the first command is activated which allows the free translation of the traction slide 3 along the sliding guide 6. In this first unlocking position, the movement in the space of the support structure 2 is prevented. The surgeon can thus freely move the slide along the sliding guide 6 and position it, more quickly, along said sliding guide in the desired position. Such free and rougher movement usually takes place in the pre-operative phase, prior to binding the gripping body 4 to the traction slide 3.

The release lever 321 can, finally, assume a second unlocking position (illustrated in FIG. 3C) which is that of free rotational movement in the space of the support structure 2, which unlocking occurs by activating the aforementioned second command. In other words, by again acting on the handle 31, and by applying a greater pressure on the release lever 321 until a second end stop, the second command is activated which releases the movement locking system of the gas springs 8' of the actuators 8. This action allows free movement in space of the entire support structure 2, which can thus be raised, lowered or rotated laterally about a vertical axis passing through the connection portion 9, while simultaneously keeping the slide 3 free to translate along the sliding guide 6. All of this is, of course, controlled by the surgeon who continues to grasp the traction slide 3, through the handle 31, and to maintain pressure on the release lever 321 to prolong the action of the second command (and thus continue to release the locking system of the actuators 8).

The three positions assumed by the release lever 321 are sequential. In other words, to switch to the second unlocking position, it is necessary to bring the release lever 321 from the locking position to the first unlocking position and from there to the second unlocking position, and in order to return from the second unlocking position to the locking position, it is necessary to position the release lever 321 in the first unlocking position and thereafter in the locking position.

At the second unlocking position, hence when the release lever 321 is at the second end stop, the automatic release of the movement of the support structure 2 in the space with respect to the connection portion 9, which is bound to the patient's resting device 100, takes place. Since the positions are sequential and the first command is activated in the passage through the first unlocking position, also the free translation of the traction slide 3 along the sliding guide 6 remains active during the movement that takes place in the second unlocking position.

It should be noted that upon release of the action by the surgeon on the lever 321, said lever automatically returns to the locking position regardless of whether it was in the first or second unlocking position.

Along the sliding guide 6, in particular along the longitudinal axis 5*a* of the central support bar 5, a plurality of holes 11 are aligned, with respective central axes 11*a* parallel to each other.

The lever system 32 further comprises a tip 322, slidingly movable along a vertical direction, orthogonal to the longitudinal axis 5*a* of the central support bar 5. The tip 322 slides inside the traction slide 3.

The first command is activated at the first unlocking position of the release lever 321: this first command causes the release lever 321 to act on the tip 322 to disengage it from a respective hole 11 of the sliding guide 6 and to allow free translation of the slide 3 along the sliding guide 6.

The lever system 32 further comprises at least one release system 324, such as for example a fluid release system, activable by the release lever 321 at its second unlocking position. The release system 324 interacts with the internal excursion locking system of the actuator 8, to unlock the spatial, in particular rotational movement around the hinge axes 9*a* and 9*b*, of the support structure 2. This sequence of phases occurs by activating the second command of the release lever 321.

The support structure 2 has a plurality of double joints 13 located at the connection points of the different components of the support structure 2 itself. Specifically, and as mentioned above, the double joints 13 are present between the central support bar 5 and the connection portion 9, in order to allow the support structure 2 to perform the required movements in space, preferably within a predefined angular range compatible with the adduction/abduction movements necessary for the correct execution of the surgical procedure. In particular, the double joints 13 allow the rotation of the support structure 2 about a vertical hinge axis 9*a*, orthogonal to the patient's resting plane, and about a horizontal hinge axis 9*b*, parallel to the patient's resting plane. As mentioned above, such spatial movement of the support structure 2 occurs following activation of the second command of the release lever 321, which activates the automatic traction unlocking.

Further double joints 13 are provided between the connection portion 9 and the actuator (or the actuators) 8, and between the actuator (or the actuators) 8 and the central support bar 5, to allow the traction slide 3 to translate along the sliding guide 6.

Going into detail, the structure of the lever system 32, which is integrated into the traction slide 3, further comprises a command drawer 323 which activates the release system 324 in fluid connection with a respective actuator 8.

The operator, by pressing the release lever 321, will act on the tip 322 by means of a plug 325 which is raised thanks to an inclined slot 326 present on the release lever 321. The tip 322, therefore, moves along the vertical direction by releasing itself from one of the holes 11 present in the sliding guide 6, in which the tip 322 is temporarily inserted; consequently, the traction slide 3, no longer bound to the sliding guide 6, can be translated along the sliding guide 6 itself and be positioned in the desired area in order to apply a rough traction to the lower limb, if required.

When the release lever 321 is pressed harder, it makes contact with the command drawer 323, which is translated along the traction direction X; in turn, the command drawer 323 activates the release system 324. The fluid, for example oil, present in the release system (or systems) 324 is put under pressure and through two tubes will act on the locking system of the actuators 8, or preferably of the gas springs 8'.

At this point, thanks to the double joints 13 that connect the connection portion 9 to the central support bar 5 and to the actuator 8, the operator can move the central support bar 5 placing it in the desired flexion/extension and/or adduction/abduction position or required by the surgical procedure (AMIS® or arthroscopic).

By loosening pressure, the release lever 321, thanks to an internal thrust spring 327, passes from the second to the first unlocking position and, consequently, the release systems 324 return to their respective rest position and the locking system of the actuators 8 (in particular of the gas springs 8') returns to act, preventing any movement of the actuators 8 and therefore any rotational movement of the support structure 2 in space. By further loosening pressure, the release lever 321, again thanks to the internal thrust spring 327, passes from the first unlocking position to the locking position, the tip 322 lowers and engages one of the holes 11 present in the sliding guide 6, preventing the traction slide 3 from sliding.

The positioning apparatus 1 further comprises a rotation group 14 associable with the traction slide 3 and connected to the gripping body 4.

The rotation group 14 has two different configurations implementable alternately on the support structure 2, depending on whether the entire apparatus 1 is to be used with a limb to be operated on or with a limb not to be operated on or depending on the surgical operation to be performed (AMIS® or arthroscopy).

Figure 4:
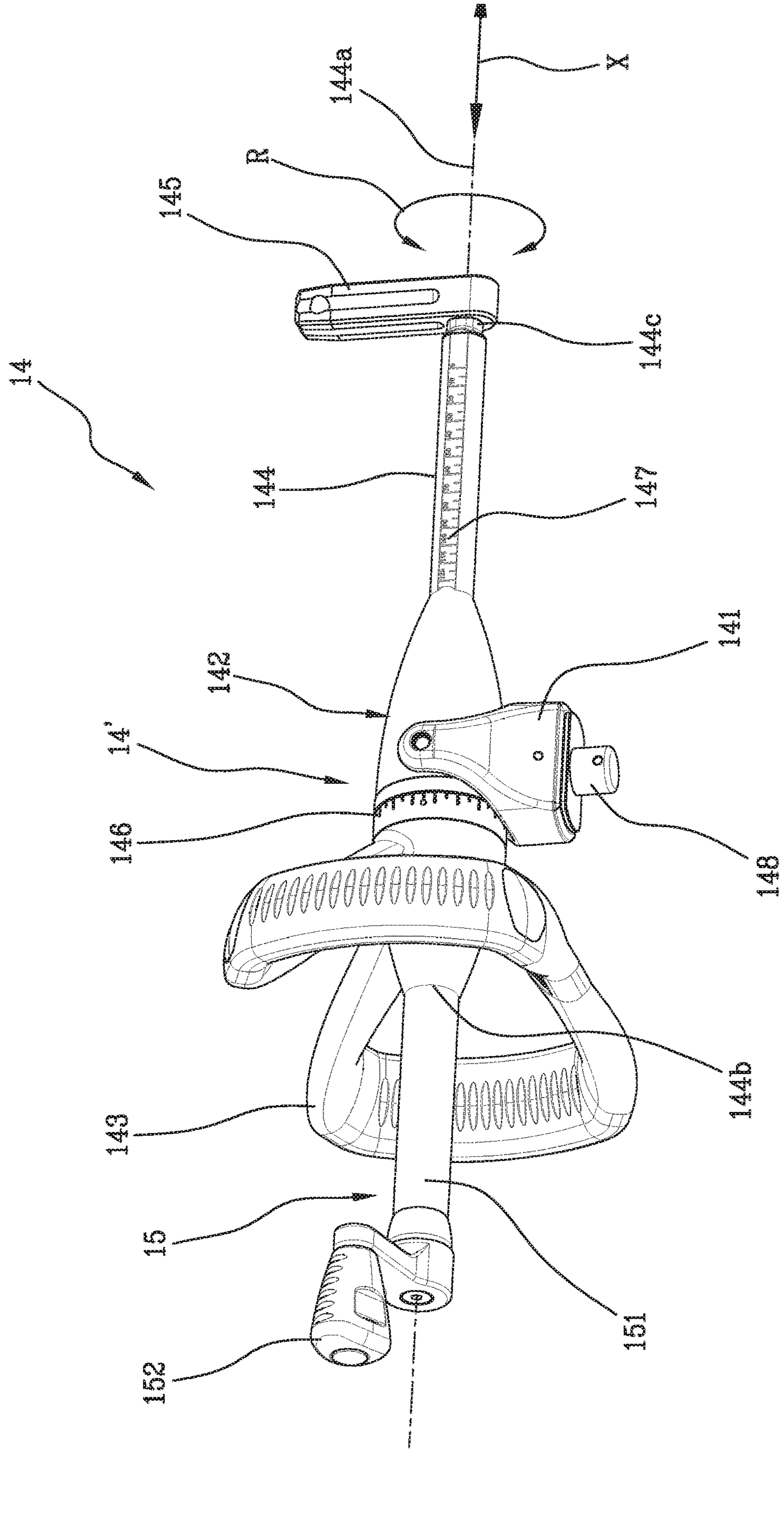
FIG. 4 illustrates a perspective view of the rotation group only, according to a first configuration, isolated from the rest of the apparatus, subject matter of the present invention.
Figure 5:
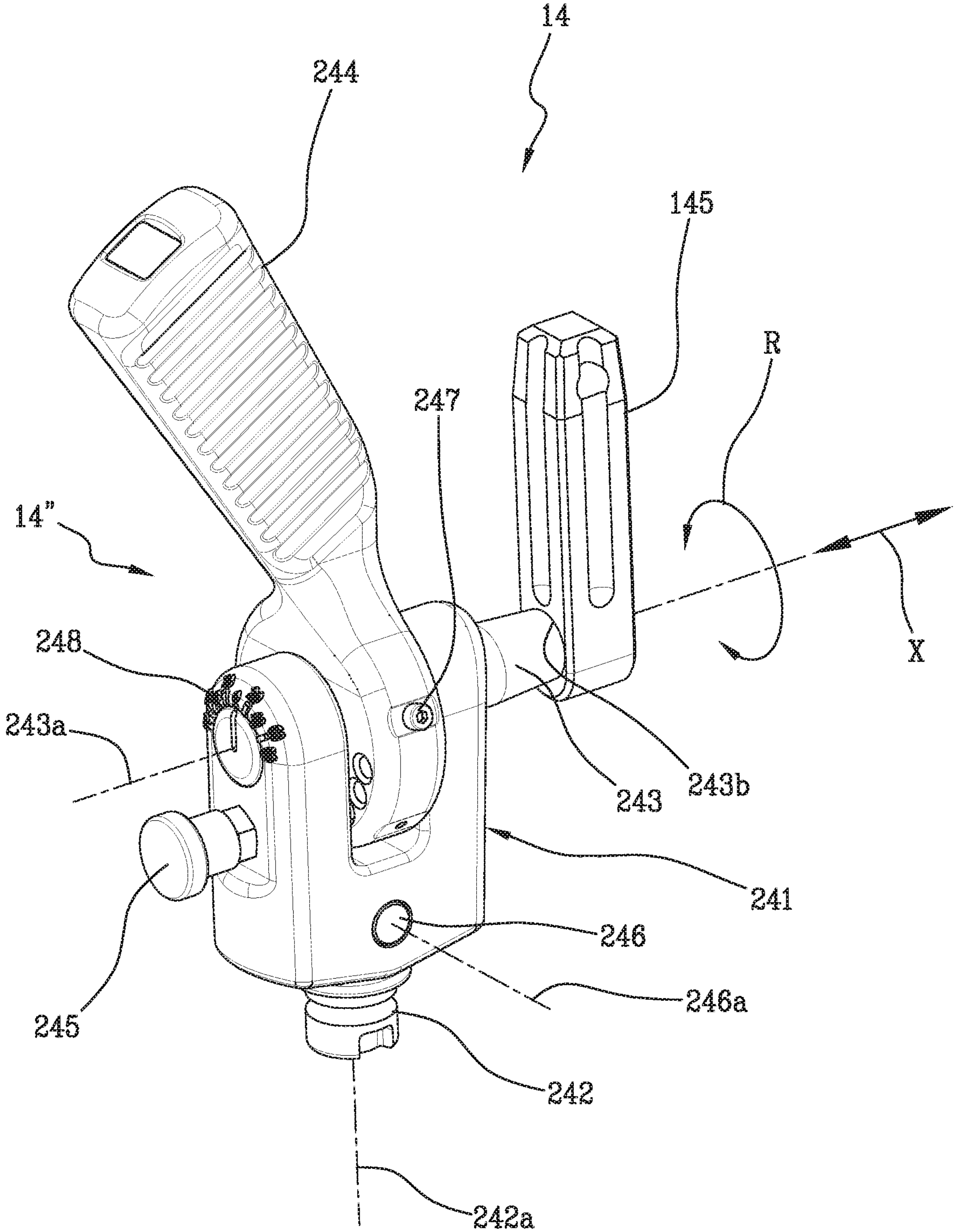
FIG. 5 illustrates a perspective view of the rotation group only, according to a second configuration, isolated from the rest of the apparatus, subject matter of the present invention.

In both configurations, the rotation group 14, shown in FIGS. 4 and 5, allows the lower limb to rotate in an internal or external direction with respect to the traction axis X itself.

In particular, according to the first configuration 14' (FIG. 4), the rotation group 14 allows rotation of the patient's lower limb in the internal or external direction in a continuous manner, being able to rotate the limb by a desired angle to best adapt to the need of the operation. In particular, the rotation group 14, in accordance with the first configuration 14' which will be described below, is preferably implemented on the support structure 2 of a positioning apparatus 2 used during AMIS® surgery (FIG. 7).

The rotation group 14, in the first configuration 14', comprises a main body 141 for the connection to the traction slide 3, through a suitable connecting shank or pin 148 insertable into a suitable housing 17 provided on the slide 3, and an oscillating group 142 that allows the rotation group 14, connected to the traction slide 3, to adapt to the natural position and inclination of the patient's lower limb.

The rotation group 14, in accordance with the first configuration 14' illustrated in FIG. 4, further comprises a command handwheel 143, used by the operator to impart the rotation required by the surgical procedure to the limb, and a graduated ring nut 146 that serves to detect the rotation angle applied to the lower limb.

The rotation is transmitted from the command handwheel 143 to the gripping body of the lower limb 4 through a rod 144 extending along a development axis 144*a*, which is connected to the handwheel 143 at a first end thereof 144*b*, and to a connection hook 145 at a second end 144*c*, opposite the first end, for hooking the gripping body 4. The latter, in turn, provides suitable means for the connection with the connection hook 145, for binding the gripping body 4 with the rotation group 14 and, therefore, with the traction slide 3.

Inside the oscillating group 142 there is a mechanism that activates or deactivates the transmission of motion from the handwheel 143 to the rod 144 that supports, at its second end 144*c*, the gripping body 4. If the operator does not act on the handwheel 143, the rod 144 does not rotate and, consequently, the patient's lower limb also does not undergo any rotation about the traction axis X. This is as a result of the mechanism within the oscillating group 142 that locks the rotation. Following the rotation applied by the operator on the handwheel 143, the aforementioned mechanism activates the rotation by transmitting the movement to the rod 144 and, therefore, to the gripping body 4 which, by wrapping the lower limb, causes the rotation thereof in the direction of rotation R applied by the operator. Once the rotation on the handwheel 143 is stopped, the mechanism within the oscillating group 142 locks the handwheel 143, the rod 144, the gripping body 4 and, therefore, the lower limb in the angular position indicated on the graduated ring nut 146.

The apparatus 1 further comprises a fine traction mechanism 15, for the millimetric movement in traction of the lower limb. Such a fine traction mechanism 15 promotes the millimetric translation of the rod 144, connectable to the gripping body 4, and thus of the lower limb.

The fine traction causes a millimetric translation of the gripping body 4, thus of the lower limb, with respect to the traction slide 3, which is in a fixed position with respect to the support structure 2.

The fine traction mechanism 15 is supported by the traction slide 3 through the traction group 14.

The fine traction mechanism 15 comprises a threaded bar 151 screwed into the rod 144 which, as noted above, is connectable to the gripping body 4 through the aforementioned connecting hook 145.

The rod 144 has a graduated scale 147, along its axial development, to control the actual movement along the traction direction X of the lower limb.

The threaded bar 151 is activated by a command element 152 which sets it in rotation: following the rotation, the threaded bar 151 meshes with the thread, located at the first end 144*b* of the rod 144, thus causing a fine, hence millimetric, translation of the rod itself 144 along the axis 144*a*.

The operator, by applying a rotation to the command element 152, for example a knob connected by means of a crossbar to the threaded bar 151, sets the threaded bar 151 itself in rotation. The latter, by screwing itself inside the rod 144, causes the graduated rod 144 to translate, which, depending on the direction of rotation chosen by the operator, imparts to the limb the required fine traction motion or applies the release thereof along the direction X.

The graduated rod 144 passes through the rotation group 14, in particular through the oscillating group 142: by means of a suitable geometry of the external section of the rod 144 and of the hole through which the same passes through the oscillating group 142, during the rotation of the limb, the rod 144 can transmit the rotation motion without imparting any secondary fine traction action.

By means of the various graduated scales on various components of the positioning apparatus 1 (on the support bar 5, on the graduated ring nut 146 and on the rod 144), at the end of the surgical procedure it is possible to reposition the limb in the initial situation and to compare the final situation with the pre-operative one.

The rotation group 14, in accordance with the second configuration 14" illustrated in FIG. 5, is adapted to rotate the lower limb of the patient in an internal or external direction with respect to the traction axis X, thus with respect to the sagittal axis of the patient, in a discrete manner, that is, according to a predefined angular pitch comprised between 15° and 25°, preferably 20°.

The rotation group 14, in accordance with the second configuration 14", comprises an oscillating body 241, connected to the traction slide 3 by means of a rotating pin 242, insertable into a suitable housing 17 provided on the slide 3, a rotation shaft 243 rotationally connected to the oscillating body 241 and carrying, at a first end 243*b*, a connection hook 145 for binding the gripping body 4 with the rotation group 14 and, therefore, with the traction slide 3.

Similarly to what happens in the first configuration, also in the second configuration 14" the oscillating body 241 allows the rotation group 14, connected to the traction slide 3, to adapt to the natural position and the inclination of the patient's lower limb contained in the gripping body 4.

The rotation group 14 in accordance with the second configuration 14" further comprises, a manoeuvring organ 244, such as a rotation lever, connected to the rotation shaft 243, capable of rotating the rotation shaft 243, about the longitudinal axis 243*a* of the shaft 243, according to a predefined angular pitch, comprised between 15° and 25°, preferably 20°. A graduated scale 248, provided on the oscillating body 241, gives an indication to the surgeon of the angular pitch set. There is also provided a locking pin 245, connected to the oscillating body 241 and engaged with the manoeuvring organ 244, adapted to lock and unlock the movement of the manoeuvring organ 244 itself and, consequently, also the rotation of the rotation shaft 243 and therefore of the limb.

The oscillating body 241 is fixed to the rotating pin 242 which allows the rotation group 14 to be connected to the traction slide 3 and to rotate by ±15° about its vertical axis 242*a* to adapt to the adduction/abduction rotation undergone by the limb during the surgical procedure, without allowing the limb to undergo an excessive and potentially damaging flexion.

The oscillating body 241 is also fixed to a pin 246 that allows the body to oscillate about an axis 246*a*, orthogonal to the vertical axis 242*a*, and to adapt to the inclination of the limb.

The operator, by acting on the locking pin 245, releases the rotation lock and is able to rotate the manoeuvring organ 244, and consequently the limb, in the required rotation direction with a discrete pitch comprised between 15° and 25°, preferably 20°. By releasing the traction on the locking pin 245, the manoeuvring organ 244, and consequently the rotation shaft 243 and the gripping body 4 carrying the patient's foot, are locked again in the position reached. The rotation of the limb is limited by the presence of two stops 247 which prevent the rotation angle established, which is ±80°, from being exceeded.

When the apparatus is to be connected to the resting device 100, it is displaced by moving it on the wheel 16 (or the wheels), located at the distal end 5*d* of the central support bar 5, and dragging it up to the proximity with the operating table.

In the pre-operative phase (set up), the apparatus is assembled by lifting the connection portion 9 from the floor level of the operating room, keeping the apparatus 1 resting only on the wheel (or wheels) 16 located at the distal end 5*d* of the central support bar 5 and the connection portion 9 is hooked to the resting device 100.

The apparatus 1 is bound to the right and/or left bracket 10 present on the resting device. This bracket, as mentioned, serves to stiffen the structure that must support the entire apparatus in suspension.

Figure 6:
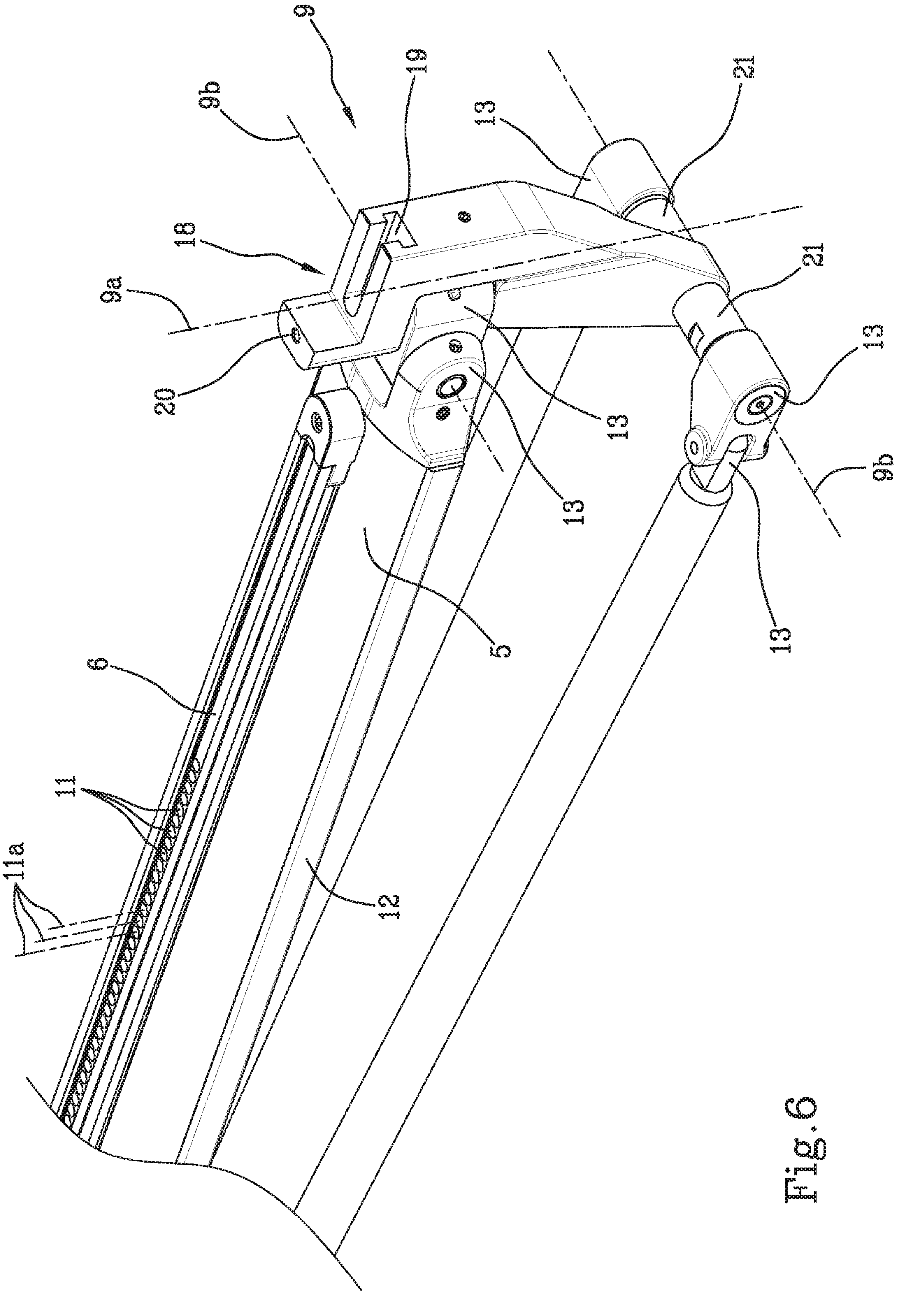
FIG. 6 shows, in perspective view, another detail of the apparatus, in particular it illustrates the portion for connecting the apparatus to a support device for a patient.

The connection portion 9 is connected to the support device 100 via a quick coupling 18 (illustrated in FIG. 6).

A constructive, but not exclusive, example provides, for example, for a groove 19 for housing a T-shaped support guide or similar provided on the bracket 10 and a cylindrical seat 20 inside which a movable pin, or other similar system, is inserted, which, entering said cylindrical seat, prevents the apparatus from sliding in the direction opposite to the hooking direction.

A double joint 13, provided with a vertical axis pin 9*a* and a horizontal axis pin 9*b*, allow the flexion/extension and adduction/abduction movements of the apparatus. Finally, two cylindrical brackets 21 acting as supports for the double joints 13 of the actuators or gas springs may be provided.

The apparatus is then integrated into a positioning system 200 comprising the positioning apparatus 1 itself, according to what is described in the present invention, a support device 100 for a patient coupled to the positioning apparatus 1 by means of at least one connecting and stiffening bracket 10.

Depending on the configuration of the rotation group used, the apparatus is used in the hip joint replacement surgical procedure through mini-invasive approach AMIS® (or DAA direct anterior approach), as a support/positioning of the non-operated limb during the same surgical procedure, or as a means of support/positioning during arthroscopic surgical procedures.

Preferably, the positioning system comprises two positioning apparatuses 1 in accordance with the present invention, one dedicated to each lower limb. Different configurations can be provided depending on the combination of the rotation group mounted on the apparatus. In fact, even if a limb is not operated on, it is advantageous for it to be supported by the apparatus in question.

Depending on the application, the device is used in the following configurations:

FIG. 7—configuration for bilateral hip prosthetic surgical procedure with AMIS® (or DAA) approach, in which the apparatus is present with a rotation group according to the first configuration 14' for both limbs of the patient. In this configuration, since both limbs are operated on, the apparatus, with the rotation group according to the first configuration 14', is used alternatively for hip surgery and as a support/positioning of the temporarily non-operated limb;

FIG. 8—configuration for arthroscopic surgical procedure, both apparatuses are present, each, with the rotation group according to the second configuration 14": one apparatus is used for the operated limb and the second apparatus is used for the support/positioning of the non-operated limb;

FIG. 9—configuration for hip prosthetic surgical procedure with AMIS® approach (or DAA), in which, depending on the operated limb, the apparatus has a rotation group according to the first configuration 14', having a fine traction system 15 for the operated limb and a rotation group according to the second configuration 14", used for the support/positioning of the non-operated limb.

The invention achieves the predetermined purposes since the described structure is lightweight thanks to the isostatic conformation of the support structure and to the absence of elements resting on the ground; this allows an easy movement in space of the apparatus, which can be so moved by the surgeon himself without the help of other operators. The absence of protruding portions resting on the ground makes the entire positioning system safer and allows a free movement of the surgeon around the operating table. All commands for the traction or rotation of the limb are immediately accessible to the surgeon and easily activated. The retention mechanisms of the movements are simplified and can be operated with simple command organs, thus making the operative procedure smooth.

Finally, the numerous graduated scales and the presence of a fine traction command make it possible to provide a positioning apparatus capable of providing a precise and simple verification of the correct position of the leg and a rapid comparison with the pre-operative position of the operated leg.

The invention claimed is:

1. An apparatus for positioning a lower limb of a patient during surgery comprising:

at least one support structure connectable through a proximal end thereof to a support device, the support structure extending along a traction axis that corresponds to a direction of traction for a patient's lower limb;

a traction slide slidingly movable on said support structure;

a gripping body for engaging a distal end of the patient's lower limb, the gripping body being connectable to said traction slide;

wherein said support structure, when connected to said support device, is suspended and comprises at least one actuator, the actuator comprising an internal excursion locking system;

wherein:

said traction slide comprises a handle and a lever system capable of unlocking the sliding of the traction slide along the support structure, wherein the lever system is movable from a locking position to a first unlocking position in response to a first command and is moveable to a second unlocking position in response to a second command, wherein the second unlocking position allows automatic unlocking and movement in space of the support structure, the excursion locking system of the at least one actuator being released in response to the first command, said actuator being in fluid connection with said traction slide.

2. The apparatus according to claim 1, wherein said support structure comprises:

a central support bar extending in a straight line along a longitudinal axis parallel with said traction axis, the central support bar having a sliding guide engageable by said traction slide, a connection portion that couples the support structure to the support device disposed at a proximal end of said central support bar and extending transversely with respect thereto;

wherein said at least one actuator extends from said connection portion to said central support bar to define a polygonal structure.

3. The apparatus according to claim 2, wherein said traction slide is bound to one or more skids sliding on said sliding guide mounted on said central bar.

4. The apparatus according to claim 2, wherein said sliding guide has a plurality of holes aligned along the longitudinal axis of said central support bar, said plurality of holes having respective central axes parallel to each other.

5. The apparatus according to claim 1, wherein said lever system comprises a release lever that can assume said locking position, said first unlocking position in response to said first command, and said second unlocking position in the space of said support structure in response to said second command, said first unlocking position and said second unlocking position of said release lever being arranged and activatable in sequence.

6. The apparatus according to claim 5, wherein said lever system further comprises a tip, wherein said tip is slidingly movable along a vertical direction orthogonal to a longitudinal axis of a central support bar, wherein said release lever, acting at its first unlocking position, disengages said tip from a respective hole of a plurality of holes present in a sliding guide and allows translation of the traction slide along the sliding guide.

7. The apparatus according to claim 5, wherein said lever system further comprises a release system activatable by said release lever at its second unlocking position, subsequent to the first unlocking position; said release system interacting with the internal excursion locking system of said actuator to unlock rotational movement in the space of said support structure.

8. The apparatus according to claim 2, wherein at least one side of said central support bar has a graduated scale for detecting the position of said traction slide along said central support bar.

9. The apparatus according to claim 8, wherein the apparatus comprises a plurality of double joints placed between the central support bar and the connection portion, between the connection portion and the actuator, and between the actuator and the central support bar, wherein the plurality of double joints allows the support structure to perform rotational movements in space and allows the traction slide to translate along the sliding guide.

10. The apparatus according to claim 1, wherein said actuator comprises at least one fluid spring, said internal excursion locking system of the actuator comprising a stem excursion locking system of the fluid spring.

11. The apparatus according to claim 1, comprising a rotation group engageable with said traction slide and connectable to said gripping body, said rotation group having a first and a second configuration alternatively or simultaneously implementable on said apparatus depending on a surgical procedure to be performed and/or depending on whether the apparatus is associated with a limb to be operated or not operated on.

12. The apparatus according to claim 11, wherein said rotation group in said first configuration is adapted to rotate said lower limb of the patient in an internal or external direction with respect to the traction axis in a continuous manner.

13. The apparatus according to claim 12, wherein said rotation group in the first configuration comprises:

a main body for connecting the rotation group to said traction slide;

an oscillating group allowing the rotation group to adapt to the position and natural inclination of the lower limb;

a command handwheel;

a rod capable of transmitting the rotation from the command handwheel to the gripping body of the lower limb;

a connection hook rigidly connected to a first end of said rod, said connection hook connecting the rotation group to said gripping body of the distal end of the lower limb; and a graduated ring nut for detecting a rotation angle applied to the lower limb.

14. The apparatus according to claim 1, comprising a fine traction mechanism for millimetric movement in traction of the lower limb, the fine traction mechanism being connectable to said gripping body and supported by said traction slide.

15. The apparatus according to claim 14, wherein said fine traction mechanism comprises a threaded bar, connectable to said gripping body, and a command element for activating a millimetric translation of the gripping body with respect to the traction slide when the traction slide is immobile with respect to the support structure.

16. The apparatus according to claim 13, wherein a threaded bar of a fine traction mechanism is screwable into said rod of the rotation group, wherein said fine traction mechanism further comprises a command element for placing said threaded bar in rotation to promote screwing with said rod and consequent translation of the rod and of the gripping body with respect to the traction slide.

17. The apparatus according to claim 13, wherein said rod is graduated and slides through said rotation group.

18. The apparatus according to claim 11, wherein said rotation group in said second configuration is adapted to rotate said lower limb of the patient in an internal or external direction with respect to the traction axis in a discrete manner and according to a predefined angular pitch comprised between 15° and 25°.

19. The apparatus according to claim 18, wherein said rotation group in the second configuration comprises:

an oscillating body connected to said traction slide by means of a rotating pin;

a rotation shaft rotationally connected to said oscillating body, said rotation shaft having a connection hook at a first end, said connection hook connecting the rotation group to said gripping body;

a maneuvering organ connected to said rotation shaft capable of rotating said rotation shaft according to a predefined angular pitch; and a locking pin engaged with the maneuvering organ adapted to lock and unlock the movement of the maneuvering organ.

20. The apparatus according to claim 1, wherein said support structure comprises, at a distal end of the support structure, at least one wheel for moving the apparatus in a pre-operative set up phase.

21. The apparatus according to claim 2, wherein said connection portion has a quick coupling.

22. A surgical positioning system comprising the positioning apparatus according to claim 1 and a support device wherein the positioning apparatus and the support device are coupled to the positioning apparatus through at least one bracket, wherein said bracket connects and stiffens said support device.

23. The surgical positioning system according to claim 22, wherein said support device is a surgical table or an adapter plane arranged to cover a surgical table.

* * * * *